(12) United States Patent
Tucci et al.

(10) Patent No.: US 6,939,883 B2
(45) Date of Patent: Sep. 6, 2005

(54) GONADOTROPIN-RELEASING HORMONE RECEPTOR ANTAGONISTS AND METHODS RELATING THERETO

(75) Inventors: Fabio Tucci, San Diego, CA (US); Patrick J. Connors, San Diego, CA (US); Yun-Fei Zhu, San Diego, CA (US); Chen Chen, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 345 days.

(21) Appl. No.: 10/211,978

(22) Filed: Aug. 2, 2002

(65) Prior Publication Data

US 2003/0119878 A1 Jun. 26, 2003

Related U.S. Application Data

(60) Provisional application No. 60/309,937, filed on Aug. 2, 2001.

(51) Int. Cl.[7] ............... A61K 31/44; C07D 401/00; C07D 421/00; C07D 211/84
(52) U.S. Cl. ............ 514/336; 514/345; 546/268.1; 546/300
(58) Field of Search ............... 514/336, 345, 514/338, 253.12, 253.11, 333, 351, 305, 341, 343, 342, 310, 313, 340, 263.22, 335; 546/268.1, 300, 273.4, 256, 281.7, 261, 133, 274.7, 279.1, 283.4, 280.4, 272.4, 143, 159; 544/360, 364, 331, 276

(56) References Cited

U.S. PATENT DOCUMENTS

| 5,780,437 A | 7/1998 | Goulet et al. .......... 514/19 |
| 5,849,764 A | 12/1998 | Goulet et al. .......... 514/337 |

FOREIGN PATENT DOCUMENTS

| WO | WO 96/38438 | 12/1996 |
| WO | WO 97/14682 | 4/1997 |
| WO | WO 97/14697 | 4/1997 |
| WO | WO 97/21435 | 6/1997 |
| WO | WO 97/21703 | 6/1997 |
| WO | WO 97/21704 | 6/1997 |
| WO | WO 97/21707 | 6/1997 |
| WO | WO 97/44037 | 11/1997 |
| WO | WO 97/44041 | 11/1997 |
| WO | WO 97/44321 | 11/1997 |
| WO | WO 97/44339 | 11/1997 |
| WO | WO 98/55116 | 12/1998 |
| WO | WO 98/55119 | 12/1998 |
| WO | WO 98/55470 | 12/1998 |
| WO | WO 98/55479 | 12/1998 |
| WO | WO 99/09033 | 2/1999 |
| WO | WO 99/33831 | 7/1999 |
| WO | WO 00/56739 | 9/2000 |
| WO | WO 01/29044 | 4/2001 |
| WO | WO 01/55119 A2 | 8/2001 |

OTHER PUBLICATIONS

Cho et al., "Discovery of a novel, potent, and orally active nonpeptide antagonist of the human luteinizing hormone-releasing hormone (LHRH) receptor," *J Med Chem.* 41(22):4190–4195, Oct. 22, 1998.

*Primary Examiner*—James O. Wilson
*Assistant Examiner*—Matthew L. Fedowitz
(74) *Attorney, Agent, or Firm*—Seed IP Law Group PLLC

(57) ABSTRACT

GnRH receptor antagonists are disclosed which have utility in the treatment of a variety of sex-hormone related conditions in both men and women. The compounds of this invention have the structure:

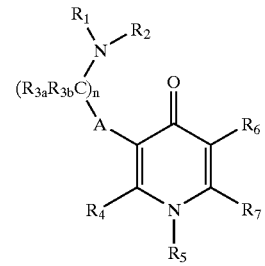

wherein A, $R_1$, $R_2$, $R_{3a}$, $R_{3b}$, $R_4$, $R_5$, $R_6$, $R_7$ and n are as defined herein, including stereoisomers, prodrugs and pharmaceutically acceptable salts thereof. Also disclosed are compositions containing a compound of this invention in combination with a pharmaceutically acceptable carrier, as well as methods relating to the use thereof for antagonizing gonadotropin-releasing hormone in a subject in need thereof.

5 Claims, No Drawings

… (1)

GONADOTROPIN-RELEASING HORMONE RECEPTOR ANTAGONISTS AND METHODS RELATING THERETO

CROSS-REFERENCE TO RELATED APPLICATION

This application claims the benefit of U.S. Provisional Patent Application No. 60/309,937, filed Aug. 2, 2001, which application is incorporated herein by reference in its entirety.

STATEMENT OF GOVERNMENT INTEREST

Partial funding of the work described herein was provided by the U.S. Government under Grant No. R43-HD38625 provided by the National Institute of Health. The U.S. Government may have certain rights in this invention.

BACKGROUND OF THE INVENTION

1. Field of the Invention

This invention relates generally to gonadotropin-releasing hormone (GnRH) receptor antagonists, and to methods of treating disorders by administration of such antagonists to a warm-blooded animal in need thereof.

2. Description of the Related Art

Gonadotropin-releasing hormone (GnRH), also known as luteinizing hormone-releasing hormone (LHRH), is a decapeptide (pGlu-His-Trp-Ser-Tyr-Gly-Leu-Arg-Pro-Gly-$NH_2$) that plays an important role in human reproduction. GnRH is released from the hypothalamus and acts on the pituitary gland to stimulate the biosynthesis and release of luteinizing hormone (LH) and follicle-stimulating hormone (FSH). LH released from the pituitary gland is responsible for the regulation of gonadal steroid production in both males and females, while FSH regulates spermatogenesis in males and follicular development in females.

Due to its biological importance, synthetic antagonists and agonists to GnRH have been the focus of considerable attention, particularly in the context of prostate cancer, breast cancer, endometriosis, uterine lciomyoma, and precocious puberty. For example, peptidic GNRH agonists, such as leuprorelin (pGlu-His-Trp-Ser-Tyr-D-Leu-Leu-Arg-Pro-NHEt), have been used to treat such conditions. Such agonists appear to function by binding to the GnRH receptor in the pituitary gonadotropins, thereby inducing the synthesis and release of gonadotropins. Chronic administration of GnRH agonists depletes gonadotropins and subsequently down-regulates the receptor, resulting in suppression of steroidal hormones after some period of time (e.g., on the order of 2–3 weeks following initiation of chronic administration).

In contrast, GnRH antagonists are believed to suppress gonadotropins from the onset, and thus have received the most attention over the past two decades. To date, some of the primary obstacles to the clinical use of such antagonists have been their relatively low bioavailability and adverse side effects caused by histamine release. However, several peptidic antagonists with low histamine release properties have been reported, although they still must be delivered via sustained delivery routes (such as subcutaneous injection or intranasal spray) due to limited bioavailability.

In view of the limitations associated with peptidic GnRH antagonists, a number of nonpeptidic compounds have been proposed. For example, Cho et al. (*J. Med. Chem.* 41:4190–4195, 1998) discloses thieno[2,3-b]pyridin-4-ones for use as GnRH receptor antagonists; U.S. Pat. Nos. 5,780, 437 and 5,849,764 teach substituted indoles as GnRH receptor antagonists (as do published PCTs WO 97/21704, 98/55479, 98/55470, 98/55116, 98/55119, 97/21707, 97/21703 and 97/21435); published PCT WO 96/38438 discloses tricyclic diazepines as GnRH receptor antagonists; published PCTs WO97/14682, 97/14697 and 99/09033 disclose quinoline and thienopyridine derivatives as GnRH antagonists; published PCTs WO 97/44037, 97/44041, 97/44321 and 97/44339 teach substituted quinolin-2-ones as GnRH receptor antagonists; and published PCT WO 99/33831 discloses certain phenyl-substituted fused nitrogen-containing bicyclic compounds as GnRH receptor antagonists.

While significant strides have been made in this field, there remains a need in the art for effective small molecule GnRH receptor antagonists. There is also a need for pharmaceutical compositions containing such GnRH receptor antagonists, as well as methods relating to the use thereof to treat, for example, sex-hormone related conditions. The present invention fulfills these needs, and provides other related advantages.

BRIEF SUMMARY OF THE INVENTION

In brief, this invention is generally directed to gonadotropin-releasing hormone (GnRH) receptor antagonists, as well as to methods for their preparation and use, and to pharmaceutical compositions containing the same. More specifically, the GnRH receptor antagonists of this invention are compounds having the following general structure (I):

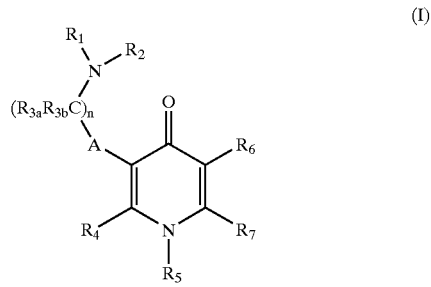

including stereoisomers, prodrugs and pharmaceutically acceptable salts thereof, wherein A, $R_1$, $R_2$, $R_{3a}$, $R_{3b}$, $R_4$, $R_5$, $R_6$, $R_7$ and n are as defined below.

The GnRH receptor antagonists of this invention have utility over a wide range of therapeutic applications, and may be used to treat a variety of sex-hormone related conditions in both men and women, as well as a mammal in general (also referred to herein as a "subject"). For example, such conditions include endometriosis, uterine fibroids, polycystic ovarian disease, hirsutism, precocious puberty, gonadal steroid-dependent neoplasia such as cancers of the prostate, breast and ovary, gonadotrophe pituitary adenomas, sleep apnea, irritable bowel syndrome, premenstrual syndrome, benign prostatic hypertrophy, contraception and infertility (e.g., assisted reproductive therapy such as in vitro fertilization). The compounds of this invention are also useful as an adjunct to treatment of growth hormone deficiency and short stature, and for the treatment of systemic lupus erythematosis. The compounds are also useful in combination with androgens, estrogens, progesterones, and antiestrogens and antiprogestogens for the treatment of endometriosis, fibroids, and in contraception, as well as in combination with an angiotensin-converting enzyme inhibitor, an angiotensin II-receptor antagonist, or a renin inhibitor for the treatment of uterine fibroids. In addition, the compounds may be used in combination with bisphosphonates and other agents for the treatment and/or prevention of disturbances of calcium, phosphate and bone metabolism, and in combination with estrogens, progesterones and/or androgens for the prevention or treatment of bone loss or hypogonadal symptoms such as hot flashes during therapy with a GnRH antagonist.

The methods of this invention include administering an effective amount of a GnRH receptor antagonist, preferably in the form of a pharmaceutical composition, to a mammal in need thereof. Thus, in still a further embodiment, pharmaceutical compositions are disclosed containing one or more GnRH receptor antagonists of this invention in combination with a pharmaceutically acceptable carrier and/or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE INVENTION

As mentioned above, the present invention is directed generally to compounds useful as gonadotropin-releasing hormone (GnRH) receptor antagonists. The compounds of this invention have the following structure (I):

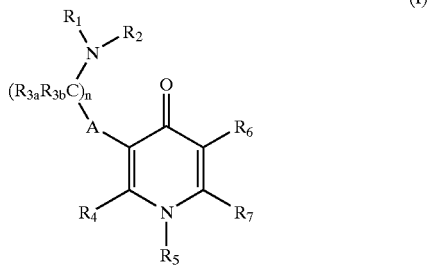

(I)

including stereoisomers, prodrugs and pharmaceutically acceptable salts thereof,
wherein:
A is O or a bond;
n is 1, 2, 3 or 4;
$R_1$ and $R_2$ are the same or different and independently hydrogen, alkyl, substituted alkyl, aryl, substituted aryl, arylalkyl, substituted arylalkyl, heterocycle, substituted heterocycle, heterocyclealkyl, substituted heterocyclealkyl, —C($R_8$)(=N$R_9$) or —C(N$R_{10}R_{11}$)(=N$R_9$);
or $R_1$ and $R_2$ taken together with the nitrogen atom to which they are attached form a heterocycle or a substituted heterocycle;
$R_{3a}$ and $R_{3b}$ are the same or different and, at each occurrence, independently hydrogen, alkyl, substituted alkyl, alkoxy, alkylthio, alkylamino, aryl, substituted aryl, arylalkyl, substituted arylalkyl, heterocycle, substituted heterocycle, heterocyclealkyl, substituted heterocyclealkyl, —COO$R_{12}$ or —CON$R_{10}R_{11}$;
or $R_{3a}$ and $R_{3b}$ taken together with the carbon atom to which they are attached form a homocycle, substituted homocycle, heterocycle or substituted heterocycle;
or $R_{3a}$ and the carbon to which it is attached taken together with $R_1$ and the nitrogen to which it is attached form a heterocycle or substituted heterocycle;

$R_4$ is hydrogen, alkyl or substituted alkyl;
$R_5$ is arylalkyl, substituted arylalkyl, heteroarylalkyl or substituted heteroarylalkyl;
$R_6$ is aryl, substituted aryl, heteroaryl or substituted heteroaryl;
$R_7$ is hydrogen, alkyl or substituted alkyl;
$R_8$, $R_9$, $R_{10}$ and $R_{11}$ are the same or different and, at each occurrence, independently hydrogen, alkyl, substituted alkyl, aryl, substituted aryl, arylalkyl, substituted arylalkyl, heterocycle, substituted heterocycle, heterocyclealkyl or substituted heterocyclealkyl; and
$R_{12}$ is hydrogen, alkyl or substituted alkyl.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl," respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl, —(CH$_2$)$_2$phenyl, —(CH$_2$)$_3$phenyl, —CH(phenyl)$_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

"Homocycle" (also referred to herein as "homocyclic ring") means a saturated or unsaturated (but not aromatic) carbocyclic ring containing from 3–7 carbon atoms, such as cyclopropane, cyclobutane, cyclopentane, cyclohexane, cycloheptane, cyclohexene, and the like.

The term "substituted" as used herein means any of the above groups (i.e., alkyl, aryl, arylalkyl, heteroaryl, heteroarylalkyl, homocycle, heterocycle and/or heterocyclealkyl) wherein at least one hydrogen atom is replaced with a substituent. In the case of an oxo substituent ("=O") two hydrogen atoms are replaced. When substituted one or more of the above groups are substituted, "substituents" within the context of this invention include halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle and heterocyclealkyl, as well as —NR$_a$R$_b$, —NR$_a$C(=O)R$_b$, —NR$_a$C(=O)NR$_a$NR$_b$, —NR$_a$C(=O)OR$_b$ —NR$_a$SO$_2$R$_b$, —C(=O)R$_a$, —C(=O)OR$_a$, —C(=O)NR$_a$R$_b$, —OC(=O) NR$_a$R$_b$, —OR$_a$, —SR$_a$, —SOR$_a$, —S(=O)$_2$R$_a$, —OS (=O)$_2$ R$_a$ and —S(=O)$_2$OR$_a$. In addition, the above substituents may be further substituted with one or more of the above substituents, such that the substituent substituted alky, substituted aryl, substituted arylalkyl, substituted heterocycle or substituted heterocyclealkyl. R$_a$ and R$_b$ in this context may be the same or different and independently hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O-alkyl) such as methoxy, ethoxy, and the like.

"Alkylthio" means an alkyl moiety attached through a sulfur bridge (i.e., —S-alkyl) such as methylthio, ethylthio, and the like.

"Alkylsulfonyl" means an alkyl moiety attached through a sulfonyl bridge (i.e., —SO$_2$-alkyl) such as methylsulfonyl, ethylsulfonyl, and the like.

"Alkylamino" and "dialkylamino" mean one or two alkyl moiety attached through a nitrogen bridge (i.e., —N-alkyl) such as methylamino, ethylamino, dimethylamino, diethylamino, and the like.

With regard to the "R$_1$R$_2$N(CR$_{3a}$R$_{3b}$)$_n$—" moiety of structure (I), n may be 1, 2, 3 or 4. Accordingly, this moiety may be represented by the following structure (i) when n is 1, (ii) when n is 2, structure (iii) when n is 3, and structure (iv) when n is 4:

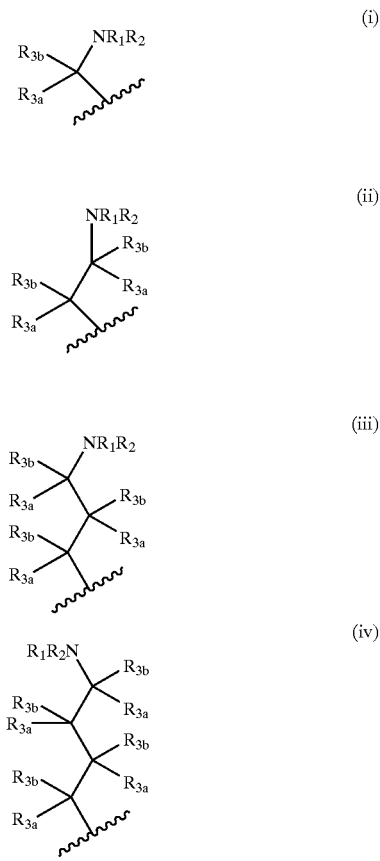

wherein each occurrence of R$_{3a}$ and R$_{3b}$ above may be the same or different, and are as defined above. For example, when each occurrence of R$_{3a}$ and R$_{3b}$ in structures (i), (ii) (iii) and (iv) is hydrogen, the "R$_1$R$_2$N(CR$_{3a}$R$_{3b}$)$_n$—" moiety has the structure R$_1$R$_2$N(CH$_2$)—, R$_1$R$_2$N(CH$_2$)$_2$—, R$_1$R$_2$N (CH$_2$)$_3$— and R$_1$R$_2$N(CH$_2$)$_4$—, respectively.

The compounds of the present invention may be prepared by known organic synthesis techniques, including the methods described in more detail in the Examples. However in general, the compounds of structure (I) above may be made by the following Reaction Schemes. All substituents in the following Reaction Schemes are as defined above unless indicated otherwise.

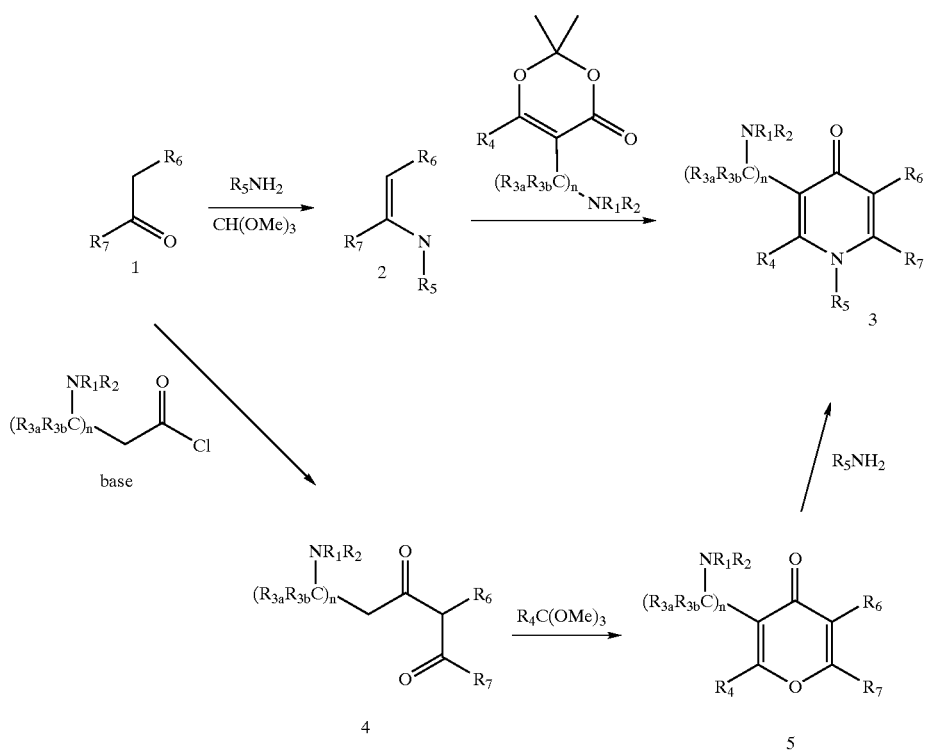

Reaction Scheme A

Ketone or aldehyde 1 and an amine are dissolved neat or with a cosolvent in an alkylorthoformate at a temperature of 0–50° C. for 12 to 36 hours to give enamine 2. Compound 2 in the presence of a substituted dioxinone in a protic solvent at elevated or reflux temperature for 1–12 hours gives product 3. Alternatively, compound 1 may be alkylated with a substituted acyl halide in the presence of a base such as sodium hydride or potassium t-butoxide in a solvent such as THF or dioxane for 1–24 hours at 0 to 50° C. to give 4. 4 in the presence of a substituted alkyl orthoester in a protic solvent at reflux for 1–24 hours gives 5. 5 and a primary amine, neat or in an inert solvent such as DMF or DMSO, are heated at an elevated temperature or at reflux temperature for 1–24 hours to give compound 3. (T. T. Tidweil, J. Org. Chem., 1998, 63, 8636)

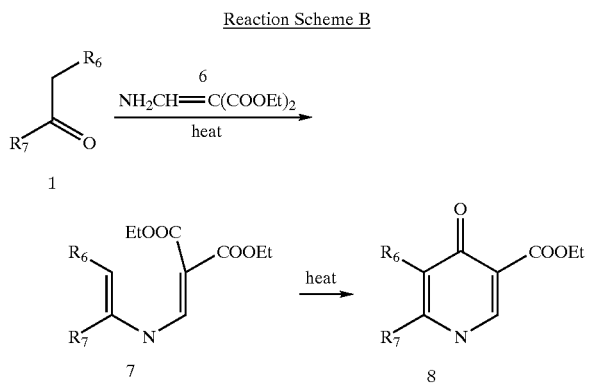

Reaction Scheme B

Compound 1 in the presence of a substituted aminocrotonate 6 is heated to 75–150° C. in a solvent such as toluene to give aminocrotonate 7 which cyclizes upon heating to give 8. (T. Kametani, J. Heterocycl. Chem., 1977, 477)

Reaction Scheme C

Meldrum's acid 9 and a substituted acetyl halide in the presence of a base such as TEA or pyridine in a solvent such as THF or dichloromethane is stirred for 1–24 hours at a temperature of 20–75° C. The reaction mix is evaporated and following a quick workup, the residue is refluxed in an alcohol to give β-keto ester 10. Compound 10 in the presence of triazine or DMFDMA followed by ammonium acetate gives compound 11. Use of a primary amine in place of ammonium acetate gives 11 with a substitution on the nitrogen. (M. Balogh, J. Heterocycl. Chem., 1980, 359; R. Kiyama, Chem. Pharm. Bull., 1995,43,450)

Scheme D

Scheme E

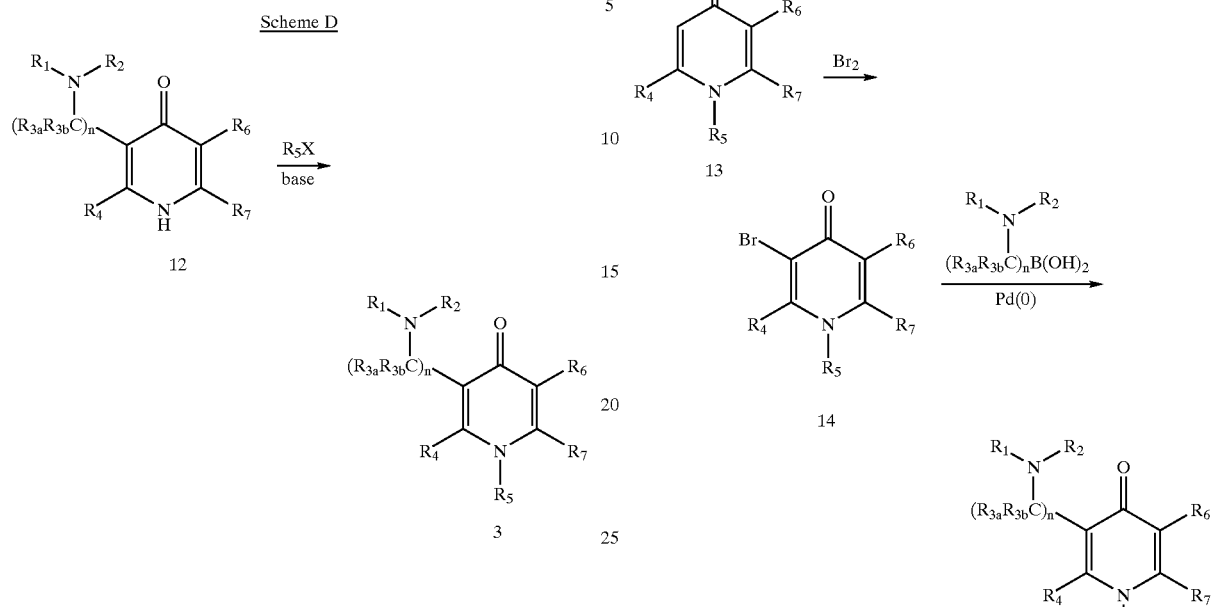

Pyridone 12 is alkylated with an alkyl halide in the presence of a base such as sodium hydride or potassium carbonate in a solvent such as DMF or acetonitrile at 0 to 50° C. for 1–24 hours to give alkylated compound 3.

Pyridone 13 may be halogenated using bromine/acetic acid, ICl in chloroform, or NIS or NBS in a solvent such as chloroform at 0–50° C. for 1–24 hours to give 14. Compound 14 and an appropriate boronic acid undergoes a Suzuki coupling to give compound 3.

Scheme F

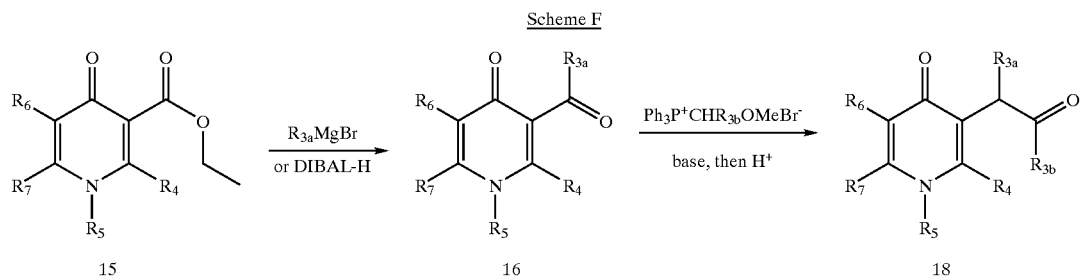

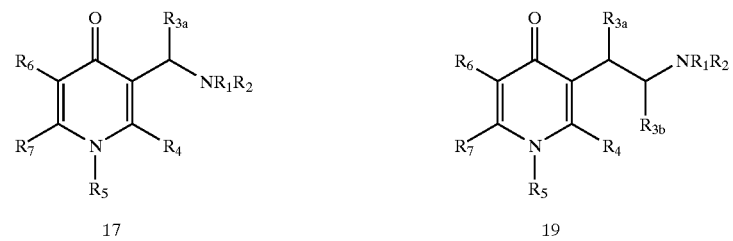

Pyridone ester 15 and a Grignard reagent at −78° C. in ether or THF for ¼ to 4 hours, or using DIBAL-H at −78° C. for approximately 2 hours in THF or ether gives 16. Reductive amination of 16 with a primary or secondary amine using a reagent such as sodium cyanoborohydride or sodium triacetoxyborohydride at 0–50° C. in an aprotic solvent such as methylene chloride for 1–24 hours gives 17. Treatment of 16 with an appropriate phosphonum salt and a base such as LDA or HMDS gives an enol that is hydrolized by treatment with an aqueous acid such as HCl to give 18. Reductive amination with an appropriate amine gives compound 19.

Compounds of structure (I) may generally be referred to as substituted 1H-pyridin-4-one compounds, representative compounds of which include the following:

3-(2-Amino-2-phenyl-ethyl)-1-(2,6-difluoro-benzyl)-2,6-dimethyl-5-(2-fluoro-3-methoxy-phenyl)-1H-pyridin-4-one;

3-(2-Amino-2-phenyl-ethyl)-1-(2,6-dichloro-benzyl)-2,6-dimethyl-5-(2-fluoro-3-methoxy-phenyl)-1H-pyridin-4-one;

3-(2-Amino-2-phenyl-ethyl)-1-(2-fluoro-6-chloro-benzyl)-2,6-dimethyl-5-(2-fluoro-3-methoxy-phenyl)-1H-pyridin-4-one;

3-(2-Amino-2-phenyl-ethyl)-1-(2-fluoro-6-trifluoromethyl-benzyl)-2,6-dimethyl-5-(2-fluoro-3-methoxy-phenyl)-1H-pyridin-4-one;

3-(2-Amino-2-phenyl-ethyl)-1-(2-fluoro-6-methylsulfonyl-benzyl)-2,6-dimethyl-5-(2-fluoro-3-methoxy-phenyl)-1H-pyridin-4-one;

3-(2-Amino-2-phenyl-ethyl)-1-(2-fluoro-benzyl)-2,6-dimethyl-5-(2-fluoro-3-methoxy-phenyl)-1H-pyridin-4-one;

3-(2-Amino-2-phenyl-ethyl)-1-(2-chloro-benzyl)-2,6-dimethyl-5-(2-fluoro-3-methoxy-phenyl)-1H-pyridin-4-one;

3-(2-Amino-2-phenyl-ethyl)-1-(2-trifluoromethyl-benzyl)-2,6-dimethyl-5-(2-fluoro-3-methoxy-phenyl)-1H-pyridin-4-one;

3-(2-Amino-2-phenyl-ethyl)-1-(2-methylsulfonyl-benzyl)-2,6-dimethyl-5-(2-fluoro-3-methoxy-phenyl)-1H-pyridin-4-one;

3-(2-Amino-2-phenyl-ethyl)-1-(2,6-difluoro-benzyl)-2,6-dimethyl-5-(2-fluoro-phenyl)-1H-pyridin-4-one;

3-(2-Amino-2-phenyl-ethyl)-1-(2,6-dichloro-benzyl)-2,6-dimethyl-5-(2-fluoro-phenyl)-1H-pyridin-4-one;

3-(2-Amino-2-phenyl-ethyl)-1-(2-fluoro-6-chloro-benzyl)-2,6-dimethyl-5-(2-fluoro-phenyl)-1H-pyridin-4-one;

3-(2-Amino-2-phenyl-ethyl)-1-(2-fluoro-6-trifluoromethyl-benzyl)-2,6-dimethyl-5-(2-fluoro-phenyl)-1H-pyridin-4-one;

3-(2-Amino-2-phenyl-ethyl)-1-(2-fluoro-6-methylsulfonyl-benzyl)-2,6-dimethyl-5-(2-fluoro-phenyl)-1H-pyridin-4-one;

3-(2-Amino-2-phenyl-ethyl)-1-(2-fluoro-benzyl)-2,6-dimethyl-5-(2-fluoro-phenyl)-1H-pyridin-4-one;

3-(2-Amino-2-phenyl-ethyl)-1-(2-chloro-benzyl)-2,6-dimethyl-5-(2-fluoro-phenyl)-1H-pyridin-4-one;

3-(2-Amino-2-phenyl-ethyl)-1-(2-trifluoromethyl-benzyl)-2,6-dimethyl-5-(2-fluoro-phenyl)-1H-pyridin-4-one;

3-(2-Amino-2-phenyl-ethyl)-1-(2-methylsulfonyl-benzyl)-2,6-dimethyl-5-(2-fluoro-phenyl)-1H-pyridin-4-one;

3-(2-Amino-2-phenyl-ethyl)-1-(2,6-difluoro-benzyl)-2,6-dimethyl-5-(2-chloro-phenyl)-1H-pyridin-4-one;

3-(2-Amino-2-phenyl-ethyl)-1-(2,6-dichloro-benzyl)-2,6-dimethyl-5-(2-chloro-phenyl)-1H-pyridin-4-one;

3-(2-Amino-2-phenyl-ethyl)-1-(2-fluoro-6-chloro-benzyl)-2,6-dimethyl-5-(2-chloro-phenyl)-1H-pyridin-4-one;

3-(2-Amino-2-phenyl-ethyl)-1-(2-fluoro-6-trifluoromethyl-benzyl)-2,6-dimethyl-5-(2-chloro-phenyl)-1H-pyridin-4-one;

3-(2-Amino-2-phenyl-ethyl)-1-(2-fluoro-6-methylsulfonyl-benzyl)-2,6-dimethyl-5-(2-chloro-phenyl)-1H-pyridin-4-one;

3-(2-Amino-2-phenyl-ethyl)-1-(2-fluoro-benzyl)-2,6-dimethyl-5-(2-chloro-phenyl)-1H-pyridin-4-one;

3-(2-Amino-2-phenyl-ethyl)-1-(2-chloro-benzyl)-2,6-dimethyl-5-(2-chloro-phenyl)-1H-pyridin-4-one;

3-(2-Amino-2-phenyl-ethyl)-1-(2-trifluoromethyl-benzyl)-2,6-dimethyl-5-(2-chloro-phenyl)-1H-pyridin-4-one;

3-(2-Amino-2-phenyl-ethyl)-1-(2-methylsulfonyl-benzyl)-2,6-dimethyl-5-(2-chloro-phenyl)-1H-pyridin-4-one;

3-(2-Amino-2-phenyl-ethyl)-1-(2,6-difluoro-benzyl)-2,6-dimethyl-5-(3-methoxy-phenyl)-1H-pyridin-4-one;

3-(2-Amino-2-phenyl-ethyl)-1-(2,6-dichloro-benzyl)-2,6-dimethyl-5-(3-methoxy-phenyl)-1H-pyridin-4-one;

3-(2-Amino-2-phenyl-ethyl)-1-(2-fluoro-6-chloro-benzyl)-2,6-dimethyl-5-(3-methoxy-phenyl)-1H-pyridin-4-one;

3-(2-Amino-2-phenyl-ethyl)-1-(2-fluoro-6-trifluoromethyl-benzyl)-2,6-dimethyl-5-(3-methoxy-phenyl)-1H-pyridin-4-one;

3-(2-Amino-2-phenyl-ethyl)-1-(2-fluoro-6-methylsulfonyl-benzyl)-2,6-dimethyl-5-(3-methoxy-phenyl)-1H-pyridin-4-one;

3-(2-Amino-2-phenyl-ethyl)-1-(2-fluoro-benzyl)-2,6-dimethyl-5-(3-methoxy-phenyl)-1H-pyridin-4-one;

3-(2-Amino-2-phenyl-ethyl)-1-(2-chloro-benzyl)-2,6-dimethyl-5-(3-methoxy-phenyl)-1H-pyridin-4-one;

3-(2-Amino-2-phenyl-ethyl)-1-(2-trifluoromethyl-benzyl)-2,6-dimethyl-5-(3-methoxy-phenyl)-1H-pyridin-4-one;

3-(2-Amino-2-phenyl-ethyl)-1-(2-methylsulfonyl-benzyl)-2,6-dimethyl-5-(3-methoxy-phenyl)-1H-pyridin-4-one;

3-(2-Amino-2-phenyl-ethyl)-1-(2,6-difluoro-benzyl)-2,6-dimethyl-5-(2-chloro-3-methoxy-phenyl)-1H-pyridin-4-one;

3-(2-Amino-2-phenyl-ethyl)-1-(2,6-dichloro-benzyl)-2,6-dimethyl-5-(2-chloro-3-methoxy-phenyl)-1H-pyridin-4-one;

3-(2-Amino-2-phenyl-ethyl)-1-(2-fluoro-6-chloro-benzyl)-2,6-dimethyl-5-(2-chloro-3-methoxy-phenyl)-1H-pyridin-4-one;

3-(2-Amino-2-phenyl-ethyl)-1-(2-fluoro-6-trifluoromethyl-benzyl)-2,6-diinethyl-5-(2-chloro-3-methoxy-phenyl)-1H-pyridin-4-one;

3-(2-Amino-2-phenyl-ethyl)-1-(2-fluoro-6-methylsulfonyl-benzyl)-2,6-dimethyl-5-(2-chloro-3-methoxy-phenyl)-1H-pyridin-4-one;

3-(2-Amino-2-phenyl-ethyl)-1-(2-fluoro-benzyl)-2,6-dimethyl-5-(2-chloro-3-methoxy-phenyl)-1H-pyridin-4-one;

3-(2-Amino-2-phenyl-ethyl)-1-(2-chloro-benzyl)-2,6-dimethyl-5-(2-chloro-3-methoxy-phenyl)-1H-pyridin-4-one;

3-(2-Amino-2-phenyl-ethyl)-1-(2-trifluoromethyl-benzyl)-2,6-dimethyl-5-(2-chloro-3-methoxy-phenyl)-1H-pyridin-4-one; and 3-(2-Amino-2-phenyl-ethyl)-1-(2-methylsulfonyl-benzyl)-2,6-dimethyl-5-(2-chloro-3-methoxy-phenyl)-1H-pyridin-4-one.

In addition, representative compounds of the present invention also include those compounds where the primary amine of the above named compounds is substituted with a substituted alkyl group or a cycloalkyl group. As described in the examples, one method of alkylating amines and amides is by reductive alkylation. There are many alternative methods well known in the chemical arts for accomplishing the reductive alkylation procedure, and there are many alternative alkylation methods. When an aldehyde, ketone, carboxylic acid, or acid chloride is treated with a primary or secondary amine in the presence of a reducing agent reductive alkylation may take place. Suitable reducing agents include (but are not limited to) sodium borohydride, sodium triacetoxyborohydride, sodium cyanoborohydride, hydrogen gas and a hydrogenation catalyst, zinc and hydrochloric acid, iron pentacarbonyl and alcoholic potassium hydroxide, formic acid, pyridine borohydride. Amines and amides may also be alkylated by the reaction of formaldehyde and a Mannich base or by the nucleophilic displacement of an alkyl halide or other leaving groups. As an example, the Mitsunobu reaction allows the alkylation of amines with primary or secondary alcohols and carboxylic acids by activation of the hydroxyl group with triphenylphosphine to form the leaving group triphenylphoshine oxide. Other commonly used alkylation methods are described in March, Advanced Organic Chemistry, 4th Ed., pp 1276–1277 (1992).

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. Compounds of structure (I) may also possess axial chirality, which may result in atropisomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The effectiveness of a compound as a GnRH receptor antagonist may be determined by various assay methods. Suitable GnRH antagonists of this invention are capable of inhibiting the specific binding of GnRH to its receptor and antagonizing activities associated with GnRH. For example, inhibition of GnRH stimulated LH release in immature rats may be measured according to the method of Vilchez-Martinez (*Endocrinology* 96:1130–1134, 1975). Briefly, twenty-five day old male Spraque-Dawley rats are administered an GnRH antagonist in saline or other suitable formulation by oral gavage, sub-cutaneous injection, or intravenous injection. This is followed by sub-cutaneous injection of 200 ng GnRH in 0.2 ml saline. Thirty minutes after the last injection, the animals are decapitated and trunk blood collected. After centrifugation, the separated plasma is stored at −20° C. until determination of the LH and FSH by radioimmunoassay. Other techniques for determining the activity of GnRH receptor antagonists are well known in the field, such as the use of cultured pituitary cells for measuring GnRH activity (Vale et al., *Endocrinology* 91:562–572, 1972), and a technique for measuring radioligand binding to rat pituitary membranes (Perrin et al., *Mol. Pharmacol.* 23:44–51, 1983).

For example, effectiveness of a compound as a GnRH receptor antagonist may be determined by one or more of the following assays.

Rat Anterior Pituitary Cell Culture Assay of GnRH Antagonists

Anterior pituitary glands are collected from 7-week-old female Sprague-Dawley rats and the harvested glands digested with collagenase in a dispersion flask for 1.5 hr at 37° C. After collagenase digestion, the glands are further digested with neuramimidase for 9 min at 37° C. The digested tissue is then washed with 0.1% BSA/McCoy's 5A medium, and the washed cells suspended in 3% FBS/0.1 BSA/McCoy's SA medium and plated into 96-well tissue culture plates at a cell density of 40,000 cells per well in 200 μl medium. The cells are then incubated at 37° C. for 3 days. One pituitary gland normally yields one 96-well plate of cells, which can be used for assaying three compounds. For assay of an GnRH antagonist, the incubated cells are first washed with 0.1% BSA/McCoy's 5A medium once, followed by addition of the test sample plus 1 nM GnRH in 200 μl 0.1% BSA/McCoy's 5A medium in triplicate wells. Each sample is assayed at 5-dose levels to generate a dose-response curve for determination of its potency on the inhibition of GnRH stimulated LH and/or FSH release. After 4-hr incubation at 37° C., the medium is harvested and the level of LH and/or FSH secreted into the medium determined by RIA.

RIA of LH and FSH

For determination of the LH levels, each sample medium is assayed in duplicates and all dilutions are done with RIA buffer (0.01M sodium phosphate buffer/0.15M NaCl/1% BSA/0.01% NaN3, pH 7.5) and the assay kit is obtained from the Nation Hormone and Pituitary Program supported by NIDDK. To a 12×75 mm polyethylene test tube is added 100 μl of sample medium diluted 1:5 or rLH standard in RIA buffer and 100 μl of [125I]-labeled rLH (~30,000 cpm) plus 100 μl of rabbit anti-rLH antibody diluted 1:187,500 and 100 μl RIA buffer. The mixture is incubated at room temperature over-night. In the next day, 100 μl of goat anti-rabbit IgG diluted 1:20 and 100 μl of normal rabbit serum diluted 1:1000 are added and the mixture incubated for another 3 hr at room temperature. The incubated tubes are then centrifuged at 3,000 rpm for 30 min and the supernatant removed by suction. The remaining pellet in the tubes is counted in a gamma-counter. RIA of FSH is done in a similar fashion as the assay for LH with substitution of the LH antibody by the FSH antibody diluted 1:30,000 and the labeled rLH by the labeled rFSH.

Radio-Iodination of GnRH Peptide

The GnRH analog is labeled by the chloramine-T method. To 10 μg of peptide in 20 μl of 0.5M sodium phosphate buffer, pH 7.6, is added 1 mCi of Na125I, followed by 22.5 μg chloramine-T and the mixture vortexed for 20 sec. The reaction is stopped by the addition of 60 μg sodium metabisulfite and the free iodine is removed by passing the iodinated mixture through a C-8 Sep-Pak cartridge (Millipore Corp., Milford, Mass.). The peptide is eluted with a small volume of 80% acetonitrile/water. The recovered labeled peptide is further purified by reverse phase HPLC on a Vydac C-18 analytical column (The Separations Group, Hesperia, Calif.) on a Beckman 334 gradient HPLC system using a gradient of acetonitrile in 0.1% TFA. The purified radioactive peptide is stored in 0.1% BSA/20% acetonitrile/0.1% TFA at −80° C. and can be used for up to 4 weeks.

GnRH Receptor Membrane Binding Assay

Cells stably, or transiently, transfected with GnRH receptor expression vectors are harvested, resuspended in 5% sucrose and homogenized using a polytron homogenizer (2×15 sec). Nucleii are removed by centrifugation (3000×g for 5 min.), and the supernatant centrifuged (20,000×g for 30 min, 4° C.) to collect the membrane fraction. The final membrane preparation is resuspended in binding buffer (10 mM Hepes (pH 7.5), 150 mM NaCl, and 0.1% BSA) and stored at −70° C. Binding reactions are performed in a Millipore MultiScreen 96-well filtration plate assembly with polyethylenimine coated GF/C membranes. The reaction is initiated by adding membranes (40 ug protein in 130 ul binding buffer) to 50 ul of [$^{125}$I]-labeled GnRH peptide (~100,000 cpm), and 20 ul of competitor at varying concentrations. The reaction is terminated after 90 minutes by application of vacuum and washing (2×) with phosphate buffered saline. Bound radioactivity is measured using 96-well scintillation counting (Packard Topcount) or by removing the filters from the plate and direct gamma counting. $K_i$ values are calculated from competition binding data using non-linear least squares regression using the Prism software package (GraphPad Software).

Activity of GnRH receptor antagonists are typically calculated from the $IC_{50}$ as the concentration of a compound necessary to displace 50% of the radiolabeled ligand from the GnRH receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff; *Biochem. Pharmacol.* 22:3099, 1973). GnRH receptor antagonists of this invention have a $K_i$ of 100 μM or less. In a preferred embodiment of this invention, the GnRH receptor antagonists have a $K_i$ of less than 10 μM, and more preferably less than 1 μM, and even more preferably less than 0.1 μM (i.e., 100 nM).

As mentioned above, the GnRH receptor antagonists of this invention have utility over a wide range of therapeutic applications, and may be used to treat a variety of sex-hormone related conditions in both men and women, as well as mammals in general. For example, such conditions include endometriosis, uterine fibroids, polycystic ovarian disease, hirsutism, precocious puberty, gonadal steroid-dependent neoplasia such as cancers of the prostate, breast and ovary, gonadotrophe pituitary adenomas, sleep apnea, irritable bowel syndrome, premenstrual syndrome, benign prostatic hypertrophy, contraception and infertility (e.g., assisted reproductive therapy such as in vitro fertilization).

The compounds of this invention are also useful as an adjunct to treatment of growth hormone deficiency and short stature, and for the treatment of systemic lupus erythematosis.

In addition, the compounds are useful in combination with androgens, estrogens, progesterones, and antiestrogens and antiprogestogens for the treatment of endometriosis, fibroids, and in contraception, as well as in combination with an angiotensin-converting enzyme inhibitor, an angiotensin II-receptor antagonist, or a renin inhibitor for the treatment of uterine fibroids. The compounds may also be used in combination with bisphosphonates and other agents for the treatment and/or prevention of disturbances of calcium, phosphate and bone metabolism, and in combination with estrogens, progesterones and/or androgens for the prevention or treatment of bone loss or hypogonadal symptoms such as hot flashes during therapy with a GnRH antagonist.

In another embodiment of the invention, pharmaceutical compositions containing one or more GnRH receptor antagonists are disclosed. For the purposes of administration, the compounds of the present invention may be formulated as pharmaceutical compositions. Pharmaceutical compositions of the present invention comprise a GNRH receptor antagonist of the present invention and a pharmaceutically acceptable carrier and/or diluent. The GNRH receptor antagonist is present in the composition in an amount which is effective to treat a particular disorder—that is, in an amount sufficient to achieve GnRH receptor antagonist activity, and preferably with acceptable toxicity to the patient. Typically, the pharmaceutical compositions of the present invention may include a GnRH receptor antagonist in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a GnRH receptor antagonist, diluents, dispersing and surface active agents, binders, and lubricants. One skilled in this art may further formulate the GnRH receptor antagonist in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating sex-hormone related conditions as discussed above. Such methods include administering of a compound of the present invention to a warm-blooded animal in an amount sufficient to treat the condition. In this context, "treat" includes prophylactic administration. Such methods include systemic administration of a GnRH receptor antagonist of this invention, preferably in the form of a pharmaceutical composition as discussed above. As used herein, systemic administration includes oral and parenteral methods of administration. For oral administration, suitable pharmaceutical compositions of GnRH receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the GnRH receptor antagonist, buffers, antioxidants, bacteriostats, and other additives commonly employed in such solutions.

The following example is provided for purposes of illustration, not limitation. In summary, the GnRH receptor antagonists of this invention may be assayed by the general methods disclosed above, while the following Examples disclose the synthesis of representative compounds of this invention.

EXAMPLE 1

Synthesis of 1-(2,6-Diflourobenzyl)-2,6-Dimethyl-3-Bromo-5-Ethoxycarbonyl-4-Pyridone

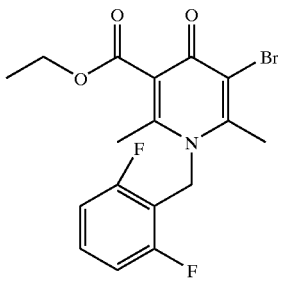

Step 1 A Ethyl-3-(2,6-difluorobenzylamino)crotonate:

2,6-Difluorobenzylamine (5.00 g, 35.0 mmol) was added to trimethyl orthoformate (88.0 mL) under $N_2$. The resulting solution was stirred at room temperature for 20 minutes. Ethyl acetoacetate (4.5 mL, 35.0 mmol) was then added dropwise and the resulting mixture stirred for 24 hours (reaction progress monitored by LC/MS). The volatiles were removed under vacuum and the product solidified upon standing. Yield 7.88 g (30.9 mmol, 88%). $^1$H NMR (CDCl$_3$, 300 MHz): 8.86 (br, 1H), 7.30–7.21 (m, 1H), 6.94–6.81 (m, 2H), 4.48 (s, 2H), 4.07 (q, J=6.9 Hz, 2H), 2.03 (s, 3H), 1.23 (t, J=6.9 Hz, 3H); LRMS m/z 256.1 (M$^+$+1).

Step 1B 1-(2,6-Difluorobenzyl)-2,6-dimethyl-3-ethoxycarbonyl-4-pyridone:

A mixture of ethyl-3-(2,6-difluorobenzylamino)crotonate (2.55 g, 10.0 mmol) and 2,2,6-trimethyl-1,3-dioxin-4-one (1.85 g, 13.0 mmol) in toluene (100 mL) was heated at reflux for 3 hours. The reaction progress was monitored by LC/MS. An additional aliquot of 2,2,6-trimethyl-1,3-dioxin-4-one (2.0 mL) was added and the reaction mixture was refluxed for another 2 hours. LC/MS indicated complete conversion to product. The mixture was cooled down and the solvent was removed in vacuo. The solid residue was triturated with diethyl ether to yield the product as a tan solid (1.37 g, 4.3 mmol, 43%). $^1$H NMR (CDCl$_3$, 300 MHz): 7.40–7.30 (m, 1H), 7.00–6.91 (m, 2H), 6.30 (s, 1H), 5.20 (s, 2H), 4.37 (q, J=6.9 Hz, 2H), 2.37 (s, 3H), 2.31 (s, 3H), 1.35 (t, J=6.9 Hz, 3H); LRMS m/z 322.1 (M$^+$+1).

Step 1C 1-(2,6-Difluorobenzyl)-2,6-dimethyl-3-bromo-5-ethoxycarbonyl-4-pyridone:

1-(2,6-Difluorobenzyl)-2,6-dimethyl-3-ethoxycarbonyl-4-pyridone (2.43 g, 7.6 mmol) was dissolved in glacial acetic acid (25 mL) and treated with bromine (490 µL, 9.5 mmol). The resulting mixture was stirred at room temperature for 8 hours and poured into ice/water. The product was extracted with dichloromethane, and the extracts were washed with 10% aqueous NaHCO$_3$, 5% aqueous Na$_2$S$_2$O$_3$ and brine. The organics were dried over anhydrous MgSO$_4$, filtered and evaporated in vacuo. The residue was triturated with diethyl ether to give the product as a white solid (1.32 g, 3.3 mmol, 43%). $^1$H NMR (CDCl$_3$, 300 MHz): 7.41–7.31 (m, 1H), 7.00–6.92 (m, 2H), 5.31 (s, 2H), 4.37 (q, J=6.9 Hz, 2H), 2.66 (s, 3H), 2.37 (s, 3H), 1.37 (t, J=6.9 Hz, 3H); LRMS m/z 400.1 (M$^+$–1), 402.1 (M$^+$+1).

EXAMPLE 2

Synthesis of 1-(2,6-Difluorobenzyl)-2,6-Dimethyl-3-(2-Fluoro-3-Methoxyphenyl)-5-[2-(2-Pyridyl)ethylaminomethyl]-4-Pyridone

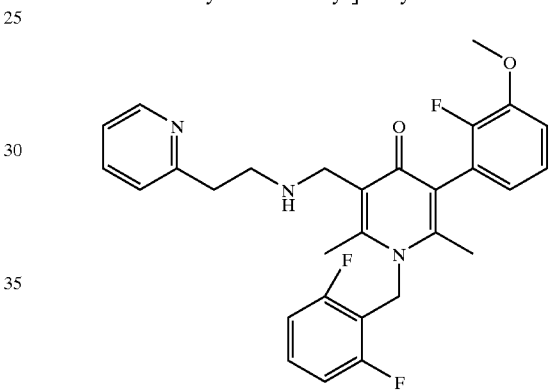

Step 2A 1-(2,6-Difluorobenzyl)-2,6-dimethyl-3-(2-fluoro-3-methoxyphenyl)-5-ethoxycarbonyl-4-pyridone:

1-(2,6-Difluorobenzyl)-2,6-dimethyl-3-bromo-5-ethoxycarbonyl-4-pyridone (1.5 g, 3.7 mmol) was evacuated in a pressure vessel with 2-fluoro-3-methoxyphenyl boronic acid (764 mg, 4.5 mmol) and tetrakis(triphenylphosphine) palladium (0) (428 mg, 370 µmol). A mixture of benzene/ethanol/1,2-dimethoxyethane (74 ml in a 10/1/11 ratio) and barium hydroxide (saturated aqueous, about 0.5M) was then added under vacuum, the vessel sealed under $N_2$, and the reaction stirred at 90° C. for twelve hours, protected from light. The organic layer was concentrated and purified using flash silica chromatography (EtOAc/hexanes-1/4 to MeOH/CH$_2$Cl$_2$-2/98), with the product eluting as the third spot. The product was dried as an amber oil (1.12 g, 2.5 mmol, 68%). $^1$H NMR (CDCl$_3$, 300 MHz) δ 6.80–7.80 (m, 6H), 5.29 (s, 2H), 4.37–4.33 (m, 2H), 3.87 (s, 3H), 3.38 (s, 3H), 2.26 (s, 3H), 1.35 (t, 3H); LCMS=446 (MH$^+$).

Step 2B 1-(2,6-Difluorobenzyl)-2,6-dimethyl-3-(2-fluoro-3-methoxyphenyl)-5-formyl-4-pyridone:

Diisobutylaluminum hydride (3.75 mmol, 3.75 ml of a 1.0M solution in hexanes) was added dropwise to a stirring solution of 1-(2,6-difluorobenzyl)-2,6-dimethyl-3-(2-fluoro-3-methoxyphenyl)-3-bromo-5-ethoxycarbonyl-4-pyridone (1.12 g, 2.5 mmol) in THF/DCM (30 mL/ 12 mL), at −78° C. under $N_2$. A suspension was formed at the end of the addition. After 1 hour, an additional aliquot of DIBAL-H (2.5 mmol, 2.5 mL of a 1.0 M solution in hexanes) was added. The reaction was stirred for 1 hour at −78° C. MeOH (50 mL) was carefully added to quench any unreacted DIBAL-H. The solution was concentrated, then partitioned between EtOAc and 1 M HCl. The organic layer was concentrated and purified using flash silica gel chromatography (100% hexanes to EtOAc/hexanes 3/2). The fourth spot which eluted was evaporated to give product as a cream colored solid. $^1$H NMR (CDCl$_3$, 300 MHz) δ 10.55 (s, 1H), 6.80–7.75 (m, 6H), 5.36 (s, 2H), 3.90 (s, 3H), 2.79 (s, 3H), 2.27 (s, 3H); LCMS=402 (MH$^+$).

Step 2C 1-(2,6-Difluorobenzyl)-2,6-dimethyl-3-(2-fluoro-3-methoxyphenyl)-5-[2-(2-pyridyl)ethylamino-4-pyridone:

Sodium borohydride (30 mg, 794 μmol) was added to a pre-mixed solution of 1-(2,6-difluorobenzyl)-2,6-dimethyl-3-(2-fluoro-3-methoxybenzyl)-5-formyl-4-pyridone (20 mg, 50 μmol) and the amine (excess) in MeOH (1 mL). Upon addition of the reducing agent, the solution quickly turned dark with the evolution of gas. Product formation was instantaneous. The crude solution was concentrated, taken up in acetonitrile, filtered and purified using a Gilson Prep-HPLC system, with the product obtained as a TFA salt in 32% yield. $^1$H NMR (CDCl$_3$, 300 MHz) δ 8.52 (d, 1H), 8.19 (t, 1H), 7.83 (d, 1H), 7.62 (t, 1H), 7.36 (m, 1H), 7.10 (t, 1H), 6.95 (m, 3H), 6.72 (t, 1H), 5.44 (s, 2H), 4.28 (s, 2H), 3.86 (s, 3H), 3.59 (m, 2H), 3.50 (m, 2H), 2.54 (s, 3H), 2.31 (s, 3H); MS=508 (MH$^+$).

The following compounds were synthesized according to above procedure.

TABLE 1

| No. | R$_6$ | R$_1$ | MS (MH$^+$) |
|---|---|---|---|
| 2-1 | 2-F-3-MeOPh | 2-PyridylCH$_2$CH$_2$ | 508 |
| 2-2 | 2-F-3-MeOPh | PhCH$_2$ | 493 |
| 2-3 | 2-F-3-MeOPh | 2-MeOPhCH$_2$ | 523 |
| 2-4 | 2-F-3-MeOPh | 2-MePhCH$_2$ | 507 |
| 2-5 | 2-F-3-MeOPh | 2-PyridylCH$_2$ | 494 |
| 2-6 | 3-MeOPh | 2-PyridylCH$_2$CH$_2$ | 490 |
| 2-7 | 3-MeOPh | PhCH$_2$ | 475 |
| 2-8 | 3-MeOPh | 2-MeOPhCH$_2$ | 505 |
| 2-9 | 3-MeOPh | 2-MePhCH$_2$ | 489 |
| 2-10 | 3-MeOPh | quinuclidinyl | 494 |
| 2-11 | 3-MeOPh | 2-methyl-5-nitroimidazol-1-ylethyl | 538 |
| 2-12 | 3-MeOPh | Me$_2$NCH$_2$CH$_2$ | 456 |
| 2-13 | 3-MeOPh | (iPr)$_2$NCH$_2$CH$_2$ | 512 |
| 2-14 | 3-MeOPh | (HOCH$_2$CH$_2$)$_2$NCH$_2$CH$_2$ | 516 |
| 2-15 | 3-MeOPh | 1-benzylpyrrolidin-3-yl | 544 |
| 2-16 | 3-MeOPh | 2-benzyl-3-oxo-3-pyrrolidin-1-ylpropyl | 586 |
| 2-17 | 3-MeOPh | 4-methylcyclohexyl | 481.2 |
| 2-18 | 3-MeOPh | 2-furylmethyl | 465.1 |
| 2-19 | 3-MeOPh | N-acetyl-lysine methyl ester | 570.3 |
| 2-20 | 3-MeOPh | indan-1-yl | 501.2 |
| 2-21 | 3-MeOPh | PhCH(CH$_3$) | 489.2 |
| 2-22 | 3-MeOPh | (CH$_3$)$_3$CCH(CH$_3$) | 469.2 |
| 2-23 | 3-MeOPh | F$_3$CCH$_2$ | 467.1 |
| 2-24 | 3-MeOPh | 2-MeO-PhCH$_2$CH$_2$ | 519.2 |
| 2-25 | 3-MeOPh | 3,4-di-(OMe)PhCH$_2$CH$_2$ | 549.2 |
| 2-26 | 3-MeOPh | n-Heptyl | 483.6 |
| 2-27 | 3-MeOPh | 3-NO$_2$PhCH$_2$ | 520.5 |
| 2-28 | 3-MeOPh | CyclopropylCH$_2$ | 439.2 |
| 2-29 | 3-MeOPh | 4-ClPhCH(CH$_3$) | 523.1 |
| 2-30 | 3-MeOPh | Et | 413.5 |
| 2-31 | 3-MeOPh | Allyl | 425.5 |
| 2-32 | 3-MeOPh | Isopropyl | 441.5 |
| 2-33 | 3-MeOPh | 2-CF$_3$-4-Cl—PhCH$_2$ | 561.2 |
| 2-34 | 3-MeOPh | 3,4-di-Cl—PhCH$_2$ | 543.1 |
| 2-35 | 3-MeOPh | 4-MeO-PhCH$_2$CH$_2$ | 519.2 |
| 2-36 | 3-MeOPh | n-Propyl | 427.1 |

TABLE 1-continued

[Structure: R1-NH-CH2 attached to pyridinone ring with R6, two methyl groups, N-benzyl with 2,6-difluoro substituents]

| No. | R₆ | R₁ | MS (MH⁺) |
|---|---|---|---|
| 2-37 | 3-MeOPh | n-Butyl | 441.5 |
| 2-38 | 3-MeOPh | 3,4,5-tri-OMe—PhCH₂ | 565.2 |
| 2-39 | 3-MeOPh | CH₃CH₂OCH₂CH₂ | 457.5 |
| 2-40 | 3-MeOPh | CH₃OCH₂(CH₃CH₂)CH | 471.5 |
| 2-41 | 2-F-3-MeOPh | 4-CH₃-Cyclohexyl-CH₂ | 499.2 |
| 2-42 | 2-F-3-MeOPh | F₃CCH₂ | 485.1 |
| 2-43 | 2-F-3-MeOPh | ((CH₃)₂CH)₂NCH₂CH₂ | 530.2 |
| 2-44 | 2-F-3-MeOPh | Cyclopropyl-CH₂ | 457.1 |
| 2-45 | 2-F-3-MeOPh | 4-Cl—PhCH₂ | 527.1 |
| 2-46 | Ph | 4-CH₃-Cyclohexyl-CH₂ | 451.2 |
| 2-47 | Ph | 2-FurylCH₂ | 435.1 |
| 2-48 | Ph | [N-acetyl lysine methyl ester side chain] | 540.2 |
| 2-49 | Ph | [indanyl group] | 471.2 |
| 2-50 | Ph | PhCH(CH₃) | 459.2 |
| 2-51 | Ph | (CH₃)₃CCH(CH₃) | 439.2 |
| 2-52 | Ph | CF₃CH₂ | 437.1 |
| 2-53 | Ph | 3,4-di-OMe—PhCH₂CH₂ | 519.2 |
| 2-54 | Ph | (iPr)₂NCH₂CH₂ | 482.2 |
| 2-55 | Ph | 2-CF₃-4-F-PhCH₂ | 531.2 |
| 2-56 | Ph | 2-F—PhCH₂CH₂ | 477.2 |
| 2-57 | Ph | (S)-2-NaphthylCH(CH₃) | 509.2 |
| 2-58 | Ph | 4-OMe-PhCH₂CH₂ | 489.6 |
| 2-59 | 2-CH₃-Thienyl | 2-FurylCH₂ | 455.5 |
| 2-60 | 2-CH₃-Thienyl | [N-acetyl lysine methyl ester side chain] | 560.6 |
| 2-61 | 2-CH₃-Thienyl | [indanyl group] | 491.1 |
| 2-62 | 2-CH₃-Thienyl | PhCH(CH₃) | 479.1 |
| 2-63 | 2-CH₃-Thienyl | (CH₃)₃CCH(CH₃) | 459.2 |
| 2-64 | 2-CH₃-Thienyl | CF₃CH₂ | 457.5 |
| 2-65 | 2-CH₃-Thienyl | 3,4-di-OMe—PhCH₂CH₂ | 539.7 |
| 2-66 | 2-CH₃-Thienyl | 4-F—PhCH₂CH₂ | 497.6 |
| 2-67 | 2-CH₃-Thienyl | (CH₃)₂CHCH₂CH₂CH(CH₃) | 473.6 |
| 2-68 | 2-CH₃-Thienyl | (iPr)₂NCH₂CH₂ | 502.7 |
| 2-69 | 2-CH₃-Thienyl | 4-Cl—PhCH(CH₃) | 514.1 |
| 2-70 | 2-CH₃-Thienyl | 2-CF₃-4-F—PhCH₂ | 551.6 |
| 2-71 | 2-CH₃-Thienyl | 2-F—PhCH₂CH₂ | 497.1 |
| 2-72 | 2-CH₃-Thienyl | [2-benzyloxy-cyclopentyl group] | 549.2 |
| 2-73 | 2-CH₃-Thienyl | PhCH₂ | 465.1 |
| 2-74 | 2-CH₃-Thienyl | 3,4-di-Cl—PhCH₂ | 535 |
| 2-75 | 2-CH₃-Thienyl | 4-MeO—PhCH₂CH₂ | 509.2 |
| 2-76 | 2-CH₃-Thienyl | n-Propyl | 417.1 |
| 2-77 | 2-CH₃-Thienyl | n-Butyl | 431.1 |
| 2-78 | 2-CH₃-Thienyl | CH₃CH₂OCH₂CH₂ | 447.6 |
| 2-79 | 2-CH₃-Thienyl | CH₃OCH₂CH(CH₂CH₃) | 461.6 |
| 2-80 | 2-CH₃-Thienyl | 2-PyridylCH₂CH₂ | 480.6 |
| 2-81 | Ph | Propyl | 397.5 |
| 2-82 | Ph | CH₃CH₂OCH₂CH₂ | 427.5 |
| 2-83 | Ph | CH₃OCH₂CH(CH₂CH₃) | 441.5 |
| 2-84 | Ph | 2-PyridylCH₂CH₂ | 460.5 |
| 2-85 | 2-F-3-MeOPh | 2-Pyridyl | 480 |
| 2-86 | 2-F-3-MeOPh | 3-Pyridyl | 480 |
| 2-87 | 2-F-3-MeOPh | 2-Pyridyl-6-Me | 494 |
| 2-88 | 2-F-3-MeOPh | 2-Pyridyl-5-Me | 494 |
| 2-89 | 2-F-3-MeOPh | 2-Pyridyl-3,5-diMe | 508 |
| 2-90 | 2-F-3-MeOPh | 2-Pyridyl-4-Cl | 514 |
| 2-91 | 2-F-3-MeOPh | 2-Pyridyl-4-Me | 494 |
| 2-92 | 2-F-3-MeOPh | 2-Pyridyl-3-Me | 494 |
| 2-93 | 2-F-3-MeOPh | [isoquinolin-1-yl] | 530 |
| 2-94 | 2-F-3-MeOPh | [quinolin-2-yl] | 530 |
| 2-95 | 2-F-3-MeOPh | 2-Pyridyl-5-F | 498 |
| 2-96 | 2-F-3-MeOPh | 2-Pyrimidyl-4-Me | 495 |
| 2-97 | 2-F-3-MeOPh | 2-Pyrimidyl-4,6-diMe | 509 |

TABLE 1-continued

[Structure: R₁-NH-CH₂ pyridinone with 2,6-difluorobenzyl group]

| No. | R₆ | R₁ | MS (MH⁺) |
|---|---|---|---|
| 2-98 | 2-F-3-MeOPh | [6-(methylthio)purin-2-yl] | 567 |
| 2-99 | 2-F-3-MeOPh | [1,2,4-triazol-3-yl] | 470 |
| 2-100 | 2-F-3-MeOPh | [5-(methylthio)-1,2,4-triazol-3-yl] | 516 |
| 2-101 | 2-F-3-MeOPh | [benzimidazol-2-yl] | 519 |
| 2-102 | 2-F-3-MeOPh | [5,6-dimethylbenzimidazol-2-yl] | 547 |
| 2-103 | 2-F-3-MeOPh | [1-methyl-5-(methylthio)-1,2,4-triazol-3-yl] | 530 |
| 2-104 | 2-F-3-MeOPh | [4-cyanoimidazol-5-yl] | 494 |

TABLE 1-continued

[Structure: R₁-NH-CH₂ pyridinone with 2,6-difluorobenzyl group]

| No. | R₆ | R₁ | MS (MH⁺) |
|---|---|---|---|
| 2-105 | 2-F-3-MeOPh | 2-ClPh | 513 |
| 2-106 | 2-F-3-MeOPh | 2-MePh | 493 |
| 2-107 | 2-F-3-MeOPh | 3-ClPh | 513 |
| 2-108 | 2-F-3-MeOPh | 3-MeOPh | 509 |
| 2-109 | 2-F-3-MeOPh | 4-MeOPh | 509 |
| 2-110 | 2-F-3-MeOPh | 4-MePh | 493 |

The following compounds were also synthesized according to the above procedure.

TABLE 2

[Structure: R₁R₂N-CH₂ pyridinone with 2,6-difluorobenzyl group]

| No. | R₆ | R₁R₂N | MS (MH⁺) |
|---|---|---|---|
| 2-111 | 2-F-3-MeOPh | 1-Pyrrolidinyl | 457.1 |
| 2-112 | 2-F-3-MeOPh | 2,6-Dimethylmorpholinyl | 501.2 |
| 2-113 | 2-CH₃-Thienyl | 1-Pyrrolidinyl | 429.5 |
| 2-114 | 2-CH₃-Thienyl | 2,6-Dimethylmorpholinyl | 473.2 |
| 2-115 | Ph | 1-Pyrrolidinyl | 409.5 |

EXAMPLE 3

Synthesis of 1-(2,6-Difluorobenzyl)-2,6-Dimethyl-3-(2-Fluoro-3-Methoxyphenyl)-5-[2-(2-Pyridyl)Ethylaminomethyl]-4-Pyridone

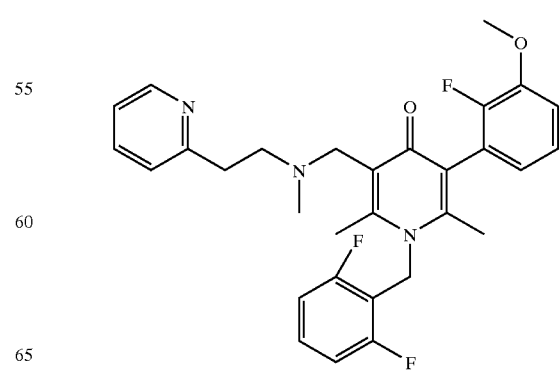

Step 3A 1-(2,6-Difluorobenzyl)-2,6-dimethyl-3-(2-fluoro-3-methoxyphenyl)-5-[N-{2-(2-pyridyl)ethyl}-N-methylaminomethyl]-4-pyridone:

Sodium triacetoxyborohydride (30 mg, 142 μmol) was added to a stirring solution of 1-(2,6-difluorobenzyl)-2,6-dimethyl-3-(2-fluoro-3-methoxybenzyl)-5-formyl-4-pyridone (20 mg, 50 μmol) and 2-(2-methylaminoethyl)pyridine (0.14 mL, 985 μmol) in dichloromethane (1 mL). The solution stirred overnight at r.t., MeOH (0.5 mL) was added and the solution concentrated, taken up in acetonitrile, filtered and purified using a Gilson Prep-HPLC system to give the product as a TFA salt in 34% yield.

The following compounds are synthesized according to above procedure.

TABLE 3

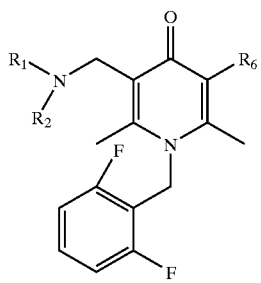

| No. | $R_6$ | $R_1R_2N-$ | MS (MH$^+$) |
|---|---|---|---|
| 3-1 | 2-F-3-MeOPh | 2-PyCH$_2$CH$_2$NMe | 522 |
| 3-2 | 2-F-3-MeOPh | PhCH$_2$NMe | 507 |
| 3-3 | 2-F-3-MeOPh | 2-PyCH$_2$NMe | 508 |
| 3-4 | 2-F-3-MeOPh | 2-PyCH$_2$NEt | 522 |
| 3-5 | 2-F-3-MeOPh | (2-PyCH$_2$)$_2$N | 585 |
| 3-6 | 3-MeOPh | 2-PyCH$_2$CH$_2$NMe | 504 |
| 3-7 | 3-MeOPh | PhCH$_2$NMe | 489 |
| 3-8 | 2-F-3-MeOPh | Et$_2$N | 516.2 |
| 3-9 | 2-CH$_3$-Thienyl | PhCH$_2$NCH$_3$ | 479.6 |
| 3-10 | 2-CH$_3$-Thienyl | 2-PyCH$_2$CH$_2$NCH$_3$ | 494.6 |
| 3-11 | 2-CH$_3$-Thienyl | Et$_2$NCH$_2$CH$_2$NCH$_3$ | 488.7 |
| 3-12 | Ph | PhCH$_2$NCH$_3$ | 459.6 |
| 3-13 | Ph | ButylNCH$_3$ | 425.5 |
| 3-14 | Ph | 2-PyCH$_2$CH$_2$NCH$_3$ | 474.2 |
| 3-15 | Ph | Et$_2$NCH$_2$CH$_2$NCH$_3$ | 468.6 |

EXAMPLE 4

Synthesis of 1-(2,6-Difluorobenzyl)-2,6-Dimethyl-3-(2-Fluoro-3-Methoxyphenyl)-5-[4-Propylpiperazinylmethyl]-4-Pyridone

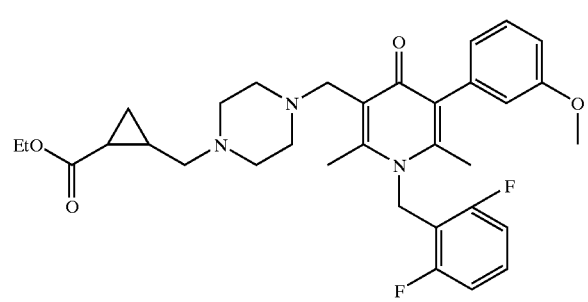

Step 4A 1-(2,6-Difluorobenzyl)-2,6-dimethyl-3-(3-methoxyphenyl)-5-formyl-4-pyridone:

1-(2,6-Difluorobenzyl)-2,6-dimethyl-3-bromo-5-formyl-pyrid-4-one (1.36 g, 3.8 mmol) stirred with 3-methoxyphenyl boronic acid (696 mg, 4.6 mmol) and tetrakis(triphenylphosphine)palladium(0) (439 mg, 380 μmol) in benzene/ethanol/DME (76 ml, 10/1/11) and barium hydroxide (30 mL, sat., aq.) under N$_2$ at 90° C., protected from light over 8 hours. The organic layer was then concentrated and purified using flash silica chromatography (ethyl acetate/hexane-1/9), giving the product as a cream-colored solid (622 mg, 1.6 mmol, 42% yield). $^1$H NMR (CDCl$_3$, 300 MHz) δ 10.55 (s, 1H), 7.41–7.31 (m, 2H), 7.00–6.74 (m, 5H), 5.35 (s, 2H), 3.81 (s, 3H), 2.79 (s, 3H), 2.25 (s, 3H); MS: 384 (MH$^+$).

Step 4B 1-(2,6-Difluorobenzyl)-2,6-dimethyl-3-(3-methoxyphenyl)-5-[piperazinylmethyl]-4-pyridone:

Sodium triacetoxyborohydride (2.75 g, 13 mmol) was added to a stirring solution of 1-(2,6-difluorobenzyl)-2,6-dimethyl-3-(3-methoxyphenyl)-5-formyl-4-pyridone (2.5 g, 6.5 mmol) and 1-boc-piperazine (1.33 g, 7.2 mmol) in CH$_2$Cl$_2$ (45 mL) at r.t. The solution was quenched with 1M KOH (5 mL) and the organic layer purified using flash silica chromatography (1% MeOH in CH$_2$Cl$_2$) to give the boc protected product as a dark brown oil. The resulting oil was treated with trifluoroacetic acid (5 mL, 6.5 mmol) in CH$_2$Cl$_2$ (20 mL) for one hour at r.t. The crude solution was concentrated and purified using flash silica chromatography (2% MeOH in CH$_2$Cl$_2$ and dried to give the product as a white foam (1.9 g, 3.4 mmol, 52% yield). $^1$H NMR (CDCl$_3$, 300 MHz) δ 7.38–7.28 (m, 2H), 6.97–6.74 (m, 5H), 5.30 (s, 2, H), 3.80 (s, 3H), 3.49 (s, 2H), 3.20–2.80 (m, 8H), 2.52 (m, 3H) 2.19 (s, 3H). MS: 568 (MH$^+$).

Step 4C 1-(2,6-Difluorobenzyl)-2,6-dimethyl-3-(3-methoxyphenyl)-5-[4-(2-ethoxycarbonylcyclopropanemethyl)piperazinylmethyl]-4-pyridone:

Sodium triacetoxyborohydride (30 mg, 141 μmol) was added to a stirring solution of 1-(2,6-difluorobenzyl)-2,6-dimethyl-3-(3-methoxyphenyl)-5-[piperazinylmethyl]-4-pyridone (50 mg, 88 μmol) with ethyl-2-formyl-1-cyclopropane carboxylate (0.05 mL, 669 μmol) in CH$_2$Cl$_2$ (1 mL). The mixture stirred at r.t. for five hours before being filtered and purified using the Gilson Prep-HPLC system, giving the product as a TFA salt (13.4 mg, 19 μmol, 22% yield). $^1$H NMR (CDCl$_3$, 300 MHz) δ 7.40–7.32 (m, 2H), 7.00–6.69 (m, 5H), 5.42 (s, 2H), 4.37 (s, 2H), 4.19–4.07 (m, 2H), 3.80 (s, 3H), 3.68–3.48 (m, 8H), 3.00–2.88 (m, 1H), 2.58 (s, 3H), 2.28 (m, 3H), 1.67–1.54 (m, 3H), 1.36–1.22 (m, 5H). MS: 580 (MH$^+$).

TABLE 4

| No. | R | MS (MH$^+$) |
|---|---|---|
| 4-1 | H | 454 |
| 4-2 | EtOCO(cPr)CH$_2$ | 580 |
| 4-3 | 5-MeFuranCH$_2$ | 548 |
| 4-4 | 3,4-MeOPhCH$_2$ | 604 |
| 4-5 | 1-NaphCH$_2$ | 594 |

TABLE 4-continued

| 4-6 | iBu | 510 |
| 4-7 | Pr | 496 |
| 4-8 | c-PrCH$_2$ | 508 |

EXAMPLE 5

Synthesis of 1-(2,6-Difluorobenzyl)-2,6-Dimethyl-3-(2-Fluoro-3-Methoxyphenyl)-5-[N-{2-(2-Pyridyl)Ethyl}-N-Methylaminomethyl]-4-Pyridone

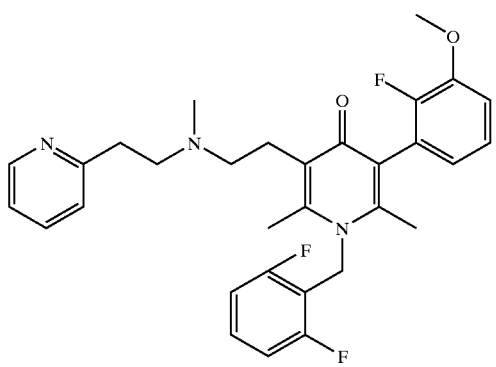

Step 5A 1-(2,6-Difluorobenzyl)-2,6-dimethyl-3-bromo-5-formyl-4-pyridone:

DIBAL (5.3 mmol, 5.3 mL of a 1.0 M solution in hexanes) was added dropwise via syringe to a stirred solution of 1-(2,6-difluorobenzyl)-2,6-dimethyl-3-bromo-5-ethoxycarbonyl-4-pyridone (1.40 g, 3.5 mmol) in THF/DCM (60 mL/20 mL), at −78° C. under N$_2$. A suspension was formed at the end of the addition. After 1 hour, an additional aliquot of DIBAL (3.0 mmol, 3.0 mL of a 1.0 M solution in hexanes) was added. The reaction was deemed complete after 1 hour at −78° C. MeOH (5 mL) was carefully added to quench any unreacted DIBAL and the mixture was partitioned between EtOAc and 1 M HCl. The organic layer was separated and washed with brine, dried over anhydrous MgSO$_4$ and filtered. Upon removal of the solvents in vacuum, the crude solid residue was triturated with Et$_2$O. The product was obtained as a beige solid (0.80 g, 2.25 mmol, 64%). $^1$H NMR (CDCl$_3$, 300 MHz): 10.55 (s, 1H), 7.40–7.33 (m, 1H), 7.00–6.93 (m, 2H), 5.38 (s, 2H), 2.78 (s, 3H), 2.69 (s, 3H); LRMS m/z 356.0 (M$^+$−1), 358.0 (M$^+$+1).

Step 5B 1-(2,6-Difluorobenzyl)-2,6-dimethyl-3-bromo-5-(2-methoxyethenyl)4-pyridone:

KHMDS (2.4 mmol, 4.8 mL of a 0.5 M solution in toluene) was added dropwise to a vigorously stirred suspension of (methoxymethyl)triphenylphosphonium chloride (771 mg, 2.25 mmol) in anhydrous THF (8 mL), at −78° C. under N$_2$. The resulting orange suspension was stirred at −78° C. for 45 min. Then, a solution of 1-(2,6-difluorobenzyl)-2,6-dimethyl-3-bromo-5-formyl-4-pyridone (534 mg, 1.50 mmol) in THF (8 mL) was added dropwise and the reaction was allowed to warm slowly to room temperature. After 1 h at room temperature, the reaction was quenched with an aqueous saturated solution of NaHCO$_3$. The organics were extracted with EtOAc (50 mL), the organic layer was separated, washed with H$_2$O and brine, dried over MgSO$_4$, filtered and evaporated under vacuum. The crude residue was utilized in the next step. LRMS m/z 384.0 (M$^+$−1), 386.0 (M$^+$+1).

Step 5C 1-(2,6-Difluorobenzyl)-2,6-dimethyl-3-bromo-5-(carbonylmethyl)4-pyridone:

The crude product above was dissolved in THF/H$_2$O (20 mL, 1:1 v/v) and to that solution TFA (5 mL) was added. The mixture was heated at reflux for 19 h. After cooling down, the reaction was extracted with CH$_2$Cl$_2$ (50 mL), washed with sat. NaHCO$_3$ and brine. After drying over MgSO$_4$, the solvent was removed under vacuum and the residue was chromatographed on silica-gel, eluting with EtOAc. The product was obtained as a pale yellow oil (431 mg, 1.16 mmol, 78% over 2 steps). $^1$H NMR (CDCl$_3$, 300 MHz) δ 9.56 (t, J=1.8 Hz, 1H), 7.38–7.33 (m, 1H), 6.98–6.93 (m, 2H), 5.37 (s, 2H), 3.83 (d, J=1.8 Hz, 2H), 2.68 (s, 3H), 2.33 (s, 3H); LRMS m/z 247.1 [M$^+$-(Br, CH$_2$CHO)], 370.0 (M$^+$−1), 372.0 (M$^+$+1).

Step 5D 1-(2,6-Difluorobenzyl)-2,6-dimethyl-3-bromo-5-[N-{2-(2-pyridyl)ethyl}-N-methylaminomethyl]-4-pyridone:

(2-Methylaminoethyl)pyridine (680 mg, 5.00 mmol) was added to a stirred solution of 1-(2,6-difluorobenzyl)-2,6-dimethyl-3-bromo-5-(carbonylmethyl)4-pyridone (430 mg, 1.16 mmol) in CH$_2$Cl$_2$ (15 mL). After 30 min., NaBH(OAc)$_3$ (1.23 g, 5.80 mmol) was added in small portions, and the resulting mixture was stirred at room temperature for 1 h. The reaction mixture was diluted with H$_2$O (15 mL) and the organic layer was separated and washed with sat. NaHCO$_3$ and brine. The organics were dried over MgSO$_4$, filtered and concentrated in vacuo. The crude was used in the next step without any further purification. Crude yield 426 mg (75%). LRMS m/z 490.0 (M$^+$−1), 492.0 (M$^+$+1).

Step 5E 1-(2,6-Difluorobenzyl)-2,6-dimethyl-3-(2-fluoro-3-methoxyphenyl)-5-[N-{2-(2-pyridyl)ethyl}-N-methylaminomethyl]4-pyridone:

The above crude bromide (98 mg, 0.20 mmol) and 3-methoxyphenyl boronic acid (36 mg, 0.24 mmol) were dissolved in DME/benzene/EtOH (11:10:1, 5 mL). To that, saturated aqueous Ba(OH)$_2$ (1.4 mL) was added and the mixture was degassed under N$_2$ for 30 minutes. Pd[Ph$_3$P]$_4$ (23 mg, 0.02 mmol) was then added and the sealed reaction vessel was stirred at 80° C. for 18 h. The reaction mixture was cooled down, extracted with EtOAc, washed with H$_2$O and brine, dried over MgSO$_4$, filtered and evaporated. The residue was purified by preparative TLC plate (0.5 mm, 20×20 cm), eluting with a CHCl$_3$/MeOH/NH$_4$OH (88.5:11.0:0.5) mixture to give product (15 mg, 0.03 mmol, 15% yield). $^1$H NMR (CDCl$_3$, 300 MHz) δ 8.50 (d, J=4.2 Hz, 1H), 7.57 (dt, J$_1$=1.8 Hz, J$_2$=7.5 Hz, 1H), 7.36–7.27 (m, 2H), 7.20 (d, J=7.5 Hz, 1H), 7.11–7.07 (m, 1H), 6.97–6.92 (m, 2H), 6.86–6.73 (m, 3H), 5.30 (s, 2H), 3.80 (s, 3H), 3.03–2.97 (m, 2H), 2.92–2.83 (m, 4H), 2.62–2.56 (m, 2H), 2.44 (s, 3H), 2.40 (s, 3H), 2.21 (s, 3H); LRMS m/z 518.3 (M$^+$1).

The following compounds are synthesized according to above procedure.

TABLE 5

[Structure showing R2-N(R1)-CH2CH2- attached to pyridinone core with R6 substituent and 2,6-difluorobenzyl N-substituent]

| No. | R6 | R1R2N | MS (MH+) |
|---|---|---|---|
| 5-1 | 2-F-3-MeOPh | 2-PyCH2CH2NMe | 536 |
| 5-2 | 3,4-CH2O2Ph | 2-PyCH2CH2NMe | 532 |
| 5-3 | 4-iPrPh | 2-PyCH2CH2NMe | 530 |
| 5-4 | 3-MeOPh | 2-PyCH2CH2NMe | 518 |

EXAMPLE 6

Synthesis of 1-(2,6-Difluorobenzyl)-2-Methyl-3-[(2R)-Amino-2-Phenylethoxyl]-5-Arylpyridin-4-One

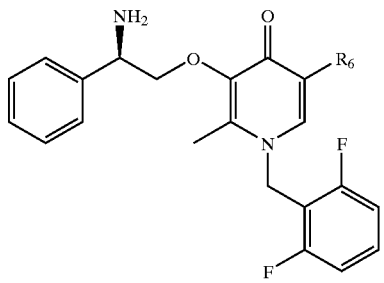

Step 6A 2-Methyl-3-[(2R)-Boc-amino-2-phenylethoxy]-4H-pyran-4-one:

Diethyl azodicarboxylate (2.36 mL, 15.0 mmol) was added dropwise to a stirred solution of Maltol (1.26 g, 10.0 mmol), triphenylphosphine (3.93 g, 15.0 mmol) and (R)-N-boc-phenylglycinol (2.37 g, 10.0 mmol) in THF (100 mL). The initial yellow color faded quickly, and the resulting colorless solution was stirred under $N_2$ for 15 h at room temperature. The solvent was removed in vacuo and the residue was purified on silica gel, eluting with a 2:1 v/v mixture of hexanes/EtOAc. The title product was obtained as a yellow oil, which was contaminated with some triphenylphosphine oxide. This mixture was carried onto the next step without any further purification. Yield=2.35 g. LRMS m/z 246 ($M^+$–boc+1), 229 (246—$NH_3$).

Step 6B 1-(2,6-Difluorobenzyl)-2-methyl-3-[(2R)-Boc-amino-2-phenylethoxy]-pyridin-4-one:

Crude 2-methyl-3-[(2R)-Boc-amino-2-phenylethoxy]-4H-pyran-4-one (1.00 g, ~2.90 mmol), 2,6-difluorobenzyl amine (700 µL, 5.8 mmol) and ethanol (3 mL) were combined and heated to 120° C. in a pressure vessel. After 16 h, the volatiles were removed in vacuo and the residue purified by column chromatography, eluting with EtOAc. The product was isolated as a white foam (204 mg, 0.43 mmol, 15%, assuming pure starting material). $^1$H NMR ($CDCl_3$-300 MHz) δ 7.42–7.19 (m, 7H); 6.98 (t, J=8.1 Hz, 2H); 6.43 (d, J=7.8 Hz, 1H); 5.06 (s, 2H); 4.87–4.83 (m, 1H); 4.06 (dd, $J_1$=9.9 Hz, $J_2$=4.2 Hz, 1H); 3.93 (dd, J=9.9 Hz, $J_2$=6.8 Hz, 1H); 2.34 (s, 3H); 1.42 (s, 9H); LRMS m/z 471.1 ($M^+$+1), 371.0 ($M^+$–boc+1).

Step 6C 1-(2,6-Difluorobenzyl)-2-methyl-3-[(2R)-Boc-amino-2-phenylethoxy]-5-bromopyridin-4-one:

N-Bromosuccinimide (79 mg, 0.44 mmol) was added to a stirred solution of 1-(2,6-difluorobenzyl)-2-methyl-3-[(2R)-Boc-amino-2-phenylethoxy]-5-bromopyridin-4-one (173 mg, 0.37 mmol) in THF (2 mL), under an atmosphere of $N_2$. The resulting mixture was refluxed for 2 h and the mixture was cooled to room temperature and partitioned between EtOAc and $H_2O$. The organic layer was separated, washed with aqueous $NaHCO_3$ and brine, dried over anhydrous $MgSO_4$, filtered and concentrated in vacuo. The product was obtained as a yellow foam (185 mg, 0.34 mmol, 92%). $^1$H NMR ($CDCl_3$-300 MHz) δ 7.76 (s, 1H); 7.47–7.19 (m, 6H); 7.00 (t, J=8.1 Hz, 2H); 5.09 (s, 2H); 4.90–4.87 (m, 1H); 4.09–4.00 (m, 2H); 2.34 (s, 3H); 1.41 (s, 9H); LRMS m/z 551.1 ($M^+$+3), 549.1 ($M^+$+1), 451.0 ($M^+$–boc+3), 449.0 ($M^+$–boc+1).

Step 6D 1-(2,6-Difluorobenzyl)-2-methyl-3-[(2R)-Boc-amino-2-phenylethoxy]-5-arylpyridin-4-one (General Procedure for Suzuki Couplings):

The aryl boronic acid (1.3 mmol) and aqueous saturated $Ba(OH)_2$ solution (7.1 mL) were added to a solution of 1-(2,6-difluorobenzyl)-2-methyl-3-[(2R)-Boc-amino-2-phenylethoxy]-5-bromopyridin-4-one (1.0 mmol) in a solvent mixture consisting of dimethoxyethane, benzene and ethanol, in a 50:45.5:4.5 ratio (20 mL), respectively. The resulting mixture was degassed by bubbling $N_2$ for about 20 minutes. Pd[$PPh_3$]$_4$ (0.1 mmol) was then added, the vessel was sealed and immersed in an oil bath at 90° C., with stirring. The reaction was monitored by TLC and LC/MS. When the starting material was consumed (typically 5–10 hours), the reaction was cooled and partitioned between EtOAc and water. The organic layer was washed with brine, dried over $MgSO_4$ and filtered. The filtrates were concentrated in vacuum and the residue was purified by column chromatography on silica gel. Yields typically range from 65–95%.

Step 6E 1-(2,6-Difluorobenzyl)-2-methyl-3-[(2R)-amino-2-phenylethoxy]-5-arylpyridin-4-one (General Procedure for N-boc Deprotections)

Trifluoroacetic acid (2 mL) was added to a solution of 1-(2,6-difluorobenzyl)-2-methyl-3-[(2R)-Boc-amino-2-phenylethoxy]-5-arylpyridin-4-one (0.09 mmol) in $CH_2Cl_2$ (2 mL) and the resulting mixture was stirred at room temperature for 2 h. TLC and LC/MS analysis showed that all starting material had been consumed. The volatiles were removed in vacuo and the residues were either purified directly by preparative HPLC or neutralized with $NH_3$ in MeOH and then purified by preparative TLC, eluting with a 88:11:1 v/v mixture of $CHCl_3$/MeOH/$NH_4OH$.

TABLE 6

[Structure: phenyl-CH(NH2)-CH2-O attached to pyridinone with R6 and 2,6-difluorobenzyl on N, methyl]

| No. | R₆ | ¹H NMR(CDCl₃, 300MHz) | MS (MH⁺) |
|---|---|---|---|
| 6-1 | 3-MeOPh | 7.55(s, 1H); 7.44–7.22(m, 8H); 7.11(dd, J₁=1.0Hz, J₂=7.7Hz, 1H); 6.99(t, J=8.1Hz, 2H); 6.86(dd, J₁=1.7Hz, J₂=8.3Hz, 1H); 5.12(s, 2H); 4.47–4.43(m, 1H); 4.19(dd, J₁=4.1Hz, J₂=9.5Hz, 1H); 4.00(dd, J₁=9.0Hz, J₂=9.5Hz, 1H); 3.83(s, 3H); 2.37(s, 3H) | 477 |
| 6-2 | 3,4-CH₂O₂Ph | 7.49(s, 1H); 7.44–7.22(m, 6H), 7.16(d, J=1.8Hz, 1H), 7.01–6.96(m, 3H); 6.83(d, J=8.1Hz, 1H); 5.95(s, 2H); 5.11(s, 2H); 4.46–4.42(m, 1H); 4.17(dd, J₁=4.0Hz, J₂=9.3Hz, 1H); 3.99(dd, J₁=8.7Hz, J₂=9.3Hz, 1H); 2.36(s, 3H) | 491 |
| 6-3 | 2-F-3-MeOPh | | 495 |

EXAMPLE 7

Synthesis of 1-(2,6-difluorobenzyl)-2,6-dimethyl-3-[N-(2-aminoethyl)aminomethyl]-5-(2-fluoro-3-methoxy)pyridin-4-one

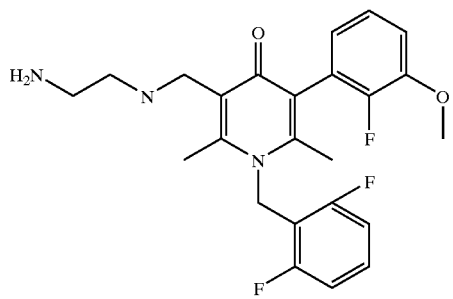

Step 7A 1-(2,6-Difluorobenzyl)-2,6-dimethyl-3-(2-fluoro-3-methoxyphenyl)-5-(2-aminoethyl)methylamino-4-pyridone Butyl(tert)-N-(2-aminoethyl)carbamate (530 mg, 3.3 mmol) was added to a stirring solution of 1-(2,6-Difluorobenzyl)-2,6-dimethyl-3-(2-fluoro-3-methoxyphenyl)-5-formyl-4-pyridone (870 mg, 2.2 mmol) and magnesium sulfate (145 mg, 1.2 mmol) in methanol (29 mL) at room temperature. The resulting mixture stirred 1 hour before addition of sodium borohydride (145 mg, 3.8 mmol). The crude reaction was concentrated in vacuo and purified by Flash silica chromatography, and dried as an amber oil. Yield 460 mg (843 μmol, 38%). LCMS m/z 546 (M⁺+1).

Trifluoroacetic acid (10 mL, 130 mmol) was added to the boc-protected diaminoethylpyridone (460 mg, 843 μmol) in dichloromethane (20 mL) and stirred for 8 h at r.t. The material was dried in vacuo as an oil, as TFA salt. Yield 470 mg (840 μmol, 99%). ¹H NMR (CDCl3, 300 MHz) δ 7.37–7.29 (m, 1H), 7.13–7.09 (m, 1H), 6.97–6.92 (m, 3H), 6.83–6.79 (m, 1H), 5.34 (s, 2H), 3.89 (s, 3H), 3.84 (s, 2H), 3.39 (m, 2H), 3.08 )(m, 2H), 2.50 (s, 3H), 2.25 (s, 3H); LCMS m/z 446 (M⁺+1).

EXAMPLE 9

Synthesis of 1-(2,6-difluorobenzyl)-2,6-dimethyl-3-[N-(2-phenyl-2-imidiazoline)methyl]-5-(2-fluror-3-methoxyphenyl)-4-pyridinone

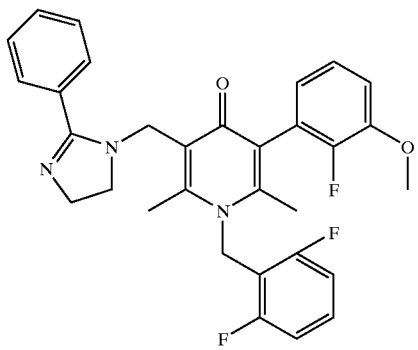

Ethyl alcohol (1 mL, 17.7 mmol) was added to 1-(2,6-difluorobenzyl)-2,6-dimethyl-3-[N-(2-aminoethyl)aminomethyl]-5-(2-fluoro-3-methoxy)-4-pyridone TFA salt (95 mg, 170 μmol) with methyl benzimidate hydrochloride (35 mg, 204 μmol), sealed in a glass pressure vessel and stirred for 2 h at 75° C. The crude material was purified using Prep-HPLC-MS, and dried in vacuo as an oil (TFA salt). Yield 30.7 mg (48 μmol, 28%). ¹H NMR (CDCl3, 300 MHz) δ 7.66–7.60 (m, 3H), 7.54–7.49 (m, 2H), 7.42–7.32 (m, 1H), 7.14–7.08 (m, 1H), 7.03–6.93 (m, 3H), 6.70–6.65 (m, 1H), 5.44 (s, 2H), 4.74 (s, 2H), 3.91 (m, 3H), 3.88 (m, 4H), 2.37 (s, 3H), 2.30 (s, 3H); LCMS m/z 532 (M⁺+1).

EXAMPLE 10

Synthesis of 1-(2,6-difluorobenzyl)-2-methyl-3-[N-(quanyl)-N'-phenylaminomethyl]-5-(2-fluoro-3-methoxyphenyl)pyridin-4-one

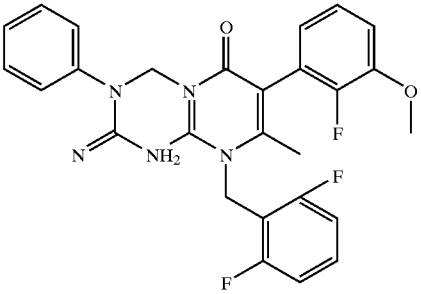

N,N'-bis-boc-1-guanylpyrazole (195 mg, 627 μmmol) was added to 1-(2,6-difluorobenzyl)-2-methyl-3-(N-phenylaminomethyl)-5-(2-fluoro-3-methoxyphenyl)pyridin-4-one (150 mg, 313 μmmol) in 1,4-dioxane (6 mL), sealed in a glass pressure vessel and stirred for 8 h at 100° C. The crude material was purified using Flash silica chromatography, and dried in vacuo as a clear oil. Yield 50 mg (69 umol, 22%).

Trifluoroacetic acid (2 mL, 26 mmol) was added to the boc-protected guanylpyridone (50 mg, 69 μmol) in dichloromethane (5 mL) and stirred for 2 h at r.t. The crude material was purified using Flash silica chromatography, and dried in vacuo as a clear yellow oil. Yield 2 mg (3.8 μmol, 5.5%). $^1$H NMR (CDCl$_3$, 300 MHz) δ 7.30–7.20 (m, 4H), 7.05–6.82 (m, 6H), 6.60–6.50 (m, 1H), 5.45 (s, 2H), 5.40–5.15 (m, 2H), 3.85 (s, 3H), 2.40 (s, 3H), 2.15 (s, 3H); LCMS m/z 521 (M$^+$+1).

It will be appreciated that, although specific embodiments of the invention have been described herein for purposes of illustration, various modifications may be made without departing from the spirit and scope of the invention. Accordingly, the invention is not limited except as by the appended claims.

All of the above U.S. patents, U.S. patent application publications, U.S. patent applications, foreign patents, foreign patent applications and non-patent publications referred to int his specification and/or listed in the Application Data Sheet are incorporated herein by reference, in their entirety.

We claim:

1. A compound having the following structure:

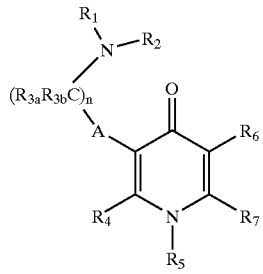

or a stereoisomer or pharmaceutically acceptable salt thereof, wherein:

A is O or a bond;

n is 1, 2, 3 or 4;

$R_1$ and $R_2$ are the same or different and independently hydrogen, alkyl, substituted alkyl, aryl, substituted aryl, arylalkyl, substituted arylalkyl, heterocycle, substituted heterocycle, heterocyclealkyl, substituted heterocyclealkyl, —C($R_8$)(=N$R_9$) or —C(N$R_{10}R_{11}$)(=N$R_9$);

or $R_1$ and $R_2$ taken together with the nitrogen atom to which they are attached form a heterocycle or a substituted heterocycle;

$R_{3a}$ and $R_{3b}$ are the same or different and, at each occurrence, independently hydrogen, alkyl, substituted alkyl, alkoxy, alkylthio, alkylamino, aryl, substituted aryl, arylalkyl, substituted arylalkyl, heterocycle, substituted heterocycle, heterocyclealkyl, substituted heterocyclealkyl, —COOR$_{12}$ or —CONR$_{10}R_{11}$;

or $R_{3a}$ and $R_{3b}$ taken together with the carbon atom to which they are attached form a homocycle, substituted homocycle, heterocycle or substituted heterocycle;

or $R_{3a}$ and the carbon to which it is attached taken together with $R_1$ and the nitrogen to which it is attached form a heterocycle or substituted heterocycle;

$R_4$ is hydrogen, alkyl or substituted alkyl;

$R_5$ is arylalkyl, substituted arylalkyl, heteroarylalkyl or substituted heteroarylalkyl;

$R_6$ is aryl, substituted aryl, heteroaryl or substituted heteroaryl;

$R_7$ is hydrogen, alkyl or substituted alkyl;

$R_8$, $R_9$, $R_{10}$ and $R_{11}$ are the same or different and, at each occurrence, independently hydrogen, alkyl, substituted alkyl, aryl, substituted aryl, arylalkyl, substituted arylalkyl, heterocycle, substituted heterocycle, heterocyclealkyl or substituted heterocyclealkyl; and $R_{12}$ is hydrogen, alkyl or substituted alkyl.

2. The compound of claim 1 wherein $R_1$ is hydrogen, alkyl, substituted alkyl, arylalkyl, substituted arylalkyl, heterocyclealkyl or substituted heterocyclealkyl.

3. The compound of claim 1 wherein $R_5$ is arylalkyl, substituted arylalkyl or heteroarylalkyl.

4. The compound of claim 1 wherein $R_6$ is substituted aryl, heteroaryl or substituted heteroaryl.

5. A pharmaceutical composition comprising a compound of claim 1 and a pharmaceutically acceptable carrier or diluent.

* * * * *